United States Patent [19]

Ranford et al.

[11] Patent Number: 4,680,029
[45] Date of Patent: Jul. 14, 1987

[54] VENA CAVAL CATHETER

[75] Inventors: Alan B. Ranford, Des Peres; David C. Fecht, Manchester, both of Mo.

[73] Assignee: Sherwood Medical Company, St. Louis, Mo.

[21] Appl. No.: 583,068

[22] Filed: Feb. 23, 1984

[51] Int. Cl.[4] ............................................. A61M 25/00
[52] U.S. Cl. ...................................... 604/280; 604/4; 604/264
[58] Field of Search .......................... 604/49, 280–285, 604/4

[56] References Cited

U.S. PATENT DOCUMENTS

| 1,518,211 | 12/1924 | Maue. | |
|---|---|---|---|
| 2,862,498 | 12/1958 | Weekes | 604/280 |
| 3,828,767 | 8/1974 | Spiroff | 128/2.05 |
| 4,129,129 | 12/1978 | Amrine | 604/49 |
| 4,309,994 | 1/1982 | Grunwald | 128/214 R |
| 4,317,452 | 3/1982 | Russo et al. | 128/350 |

OTHER PUBLICATIONS

William Harvey, "Quality Construction in a Variety of Designs", one page, both sides.
Sherwood Medical Co., "Argyle", Perfusion Product Manual, pp. 13 and 15.
C. R. Bard, "USCI", Extracorporeal Circulation Cannulae, Sec. 7, pp. 1, 8, 9, 10, 11, 12 & 14.
Sarns Inc., Ann Arbor, Mich., "Sterilized Disposable Instruments", pp. 14, 18, 20, 21, 22, 24, 26, 28 & address page.

Primary Examiner—Ferris H. Lander
Attorney, Agent, or Firm—Stanley N. Garber; Andrew J. Beck; William R. O'Meara

[57] ABSTRACT

A vena caval catheter is provided with a distal cage-like catheter tip having a cone connected to the inner side of the distal end of the tip within the cage and with the apex proximally of the distal end of the tip and coincident with the longitudinal axis of the catheter tip. The tip has a distal end and struts having smoothly contoured surfaces.

20 Claims, 7 Drawing Figures

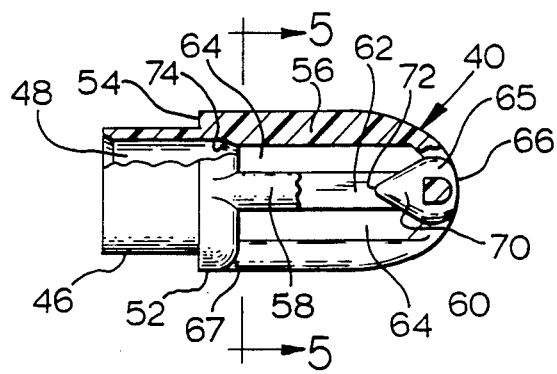
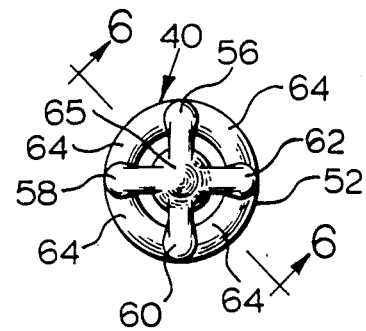
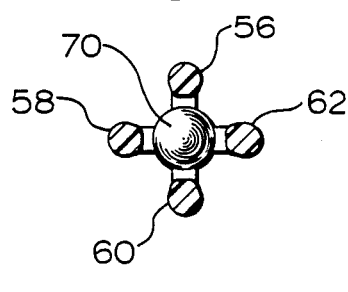
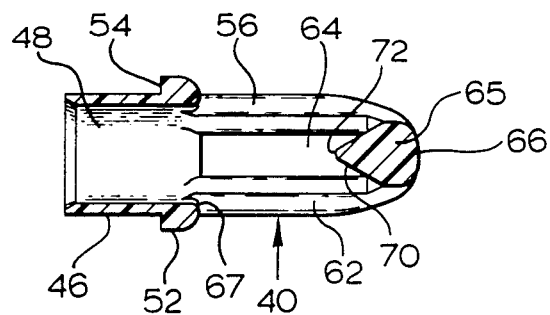
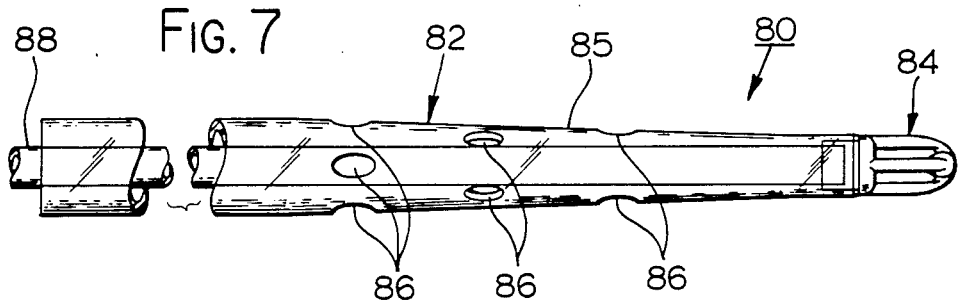

4,680,029

VENA CAVAL CATHETER

TECHNICAL FIELD

This invention relates to vena caval catheters and, more particularly, to a vena caval catheter having a tip shaped for improved blood flow characteristics.

BACKGROUND ART

As is well known, vena caval catheters are used during surgical procedures on the heart or an adjacent blood vessels to connect the vena cavae into a cardiopulmonary by-pass extracorporeal circulation system. Generally, the extracorporeal system includes a blood oxygenator, defoamer, heat exchanger to control body temperature, an air bubble trap, a particulate filter, and a blood pump for returning oxygenated blood to the arterial system of the patient.

In one standard method of employing vena caval catheters to effect venous return catheterization, two vena caval catheters are inserted independently into the atrium. One of the catheters is directed into the inferior vena cava and the other catheter is directed into the superior vena cava. Tourniquets are sometimes used to close the vena cavae about the catheters, so that substantially bloodless surgery may be performed on the heart or adjacent vessels. Venus blood from the upper extremeties of the body flows in the superior vena cava and into the tip of the vena caval or return catheter that is directed into that vena cava. Blood from the trunk and lower extremities of the patient flows in the inferior vena cava and into the tip of the return catheter disposed in that vena cava. In certain cases, a complete by-pass is not employed, for example, a single vena caval catheter may be used where the heart is not to be opened. For example, a two-stage vena caval or venous return catheter having an open end and sidewall openings may be inserted through the right atrium and into the inferior vena cava for draining venous blood into the extracorporeal circulation system. Venous blood, in such case, can flow from the inferior vena cava into the end opening of the dual-stage catheter and blood from the right atrium can flow into the openings in the sidewall of the catheter. Because the walls of the vena cava are flexible, some vena caval catheters have been provided with molded, cage-like tips so that the walls of the vena cava cannot close the inlet or tip of the catheter.

Known vena caval catheters have not been entirely satisfactory for one reason or another. The shape of the catheter tip through which blood enters the catheter has, in some cases, resulted in poor hemodynamic porperties. For example, surfaces at the tip may effect relatively high flow resistances, thus causing undesireable pressure drops as the blood flows into the catheter tip and this tends to increase blood hemolysis. In some cases, surfaces may not be washed with blood thereby increasing the danger of creating initial stages of thrombosis, especially if anitcoagulant levels become low.

DISCLOSURE OF THE INVENTION

It is therefore the object of the present invention to provide an improved vena caval catheter which reduces or obviates the above-mentioned disadvantages or problems.

A more specific object of the invention is to provide vena caval catheter having an improved tip resulting in good blood flow charactistrics so as to effect reduced pressure drops, reduced hemolysis, and reduced chance of initiating thrombosis.

In accordance with one aspect of the present invention, a vena caval catheter is provided which has a catheter tip that includes a plurality of circumferentially spaced, longitudinally extending struts connected together, a distal end having a smoothly rounded outer surface, and a generally cone-shaped portion connected to the distal end and tapering radially inwardly in the proximal direction.

These, as well as other objects and advantages of the invention, will become apparent from the following detailed description and accompanying drawings.

BRIEF DESCRIPTION OF THE DRAWINGS

FIG. 3 is an enlarged side view of the tip of the catheter of FIG. 2;

FIG. 4 is a right end view of the tip of FIG. 3;

FIG. 5 is a cross-sectional view taken along the line 5—5 of FIG. 3;

FIG. 6 is a cross-sectional view taken along the line 6—6 of FIG. 4; and

FIG. 7 is side view of a vena caval catheter in accordance with a modified embodiment of the present invention.

DETAILED DESCRIPTION OF THE PREFERRED EMBODIMENTS

Figure 1:
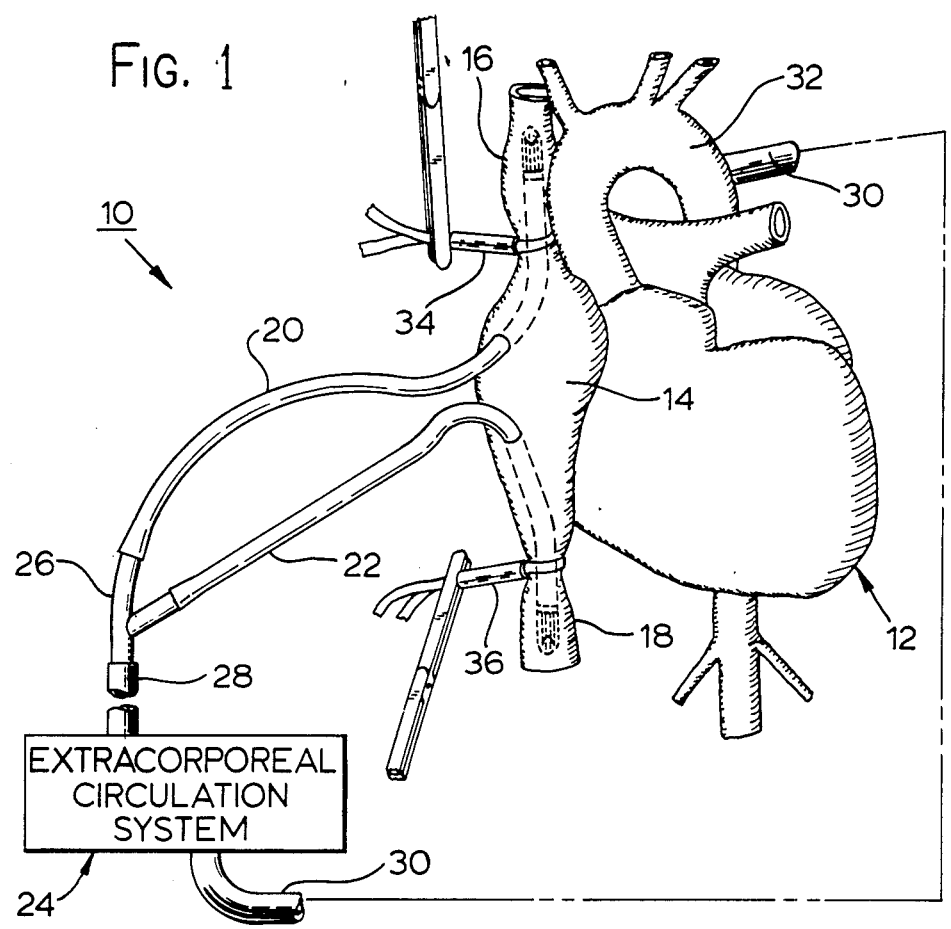
FIG. 1 is a side elevational view of certain organs of a patient including the heart connected to an extracorporeal system utilizing vena caval catheters made in accordance with the present invention.

Referring now to the drawings, and particularly to FIG. 1, there is illustrated a portion of a surgical site 10 showing a heart 12, a right atrium 14, and superior and inferior vena cavae 16 and 18, respectively. The vena cavae are connected by a pair of identical vena caval catheters 20 and 22 into a cardiopulmonary by-pass or extracorporeal circulation system indicated generally at 24. Catheters 20 and 22 are connected by a Y-connector 26 which delivers the venus blood through a tube 28 into the main components of the extracorporeal system 24. System 24 generally will include a blood oxgenator, blood defoamer, blood pump, particulate filter, a bubble trap, and a return tube such as indicated at 30, for returning oxygenated blook to the arterial system of the patient, such as by connecting tube 30 to the aorta, indicated at 32.

The walls of the atrium 14 are sealed about catheters 20 and 22 such as by conventional purse string sutures (not shown). Conventional vascular torniquets, 34 and 36 are shown closing off the vena cavae 16 and 18, respectivley, from the right atrium 14. As shown, torniquet 34 encircles and is tightened about vena cava 16 and catheter 20 while torniquet 36 is tightened about vena cava 18 and catheter 22. With this system, the heart and lungs of the patient are fully or completely bypassed so that the heart and adjacent vessels may be operated on in the dry state. Other apparatus, including other catheters such as left ventricular vent and/or atrial vent catheters, may be employed in the extracorporeal system 24 as required.

Figure 2:
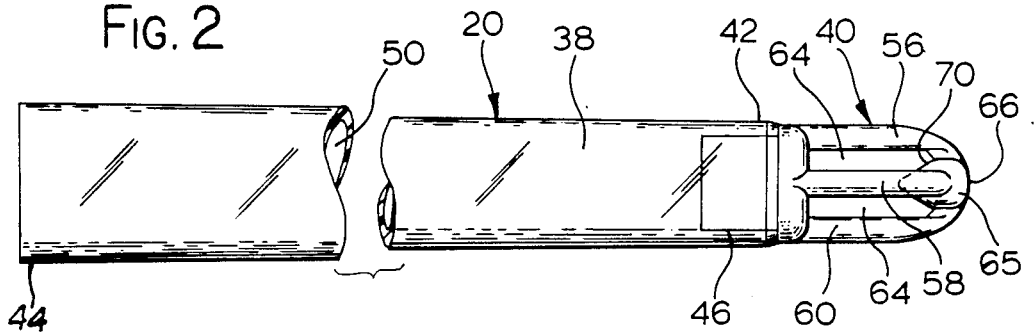
FIG. 2 is an enlarged side view of a vena caval catheter of FIG. 1.

Since the catheters 20 and 22 are identical, only catheter 20 is shown and described in detail. As seen in FIG. 2, catheter 20 includes a tube 38, and a cage-like catheter tip 40 connected to the distal end 42 of tube 38. The tube 38 may be, for example, an extruded flexible tube of a plastic material such as rubber, polyvinyl chloride, polypropylene, or other suitable plastic material. Preferably, the tube is of a transparent plastic such as of transparent polyvinyl chloride. The catheter tip 40 may be molded from a plastic material such as polyvinyl chloride, polypropylene or other suitable plastic. The proximal end 44 of tube 38 is adapted to be connected as shown in FIG. 1 to a connector such as Y connector 26. The tube 38 may be slightly tapered with the diameter of the distal end slightly narrower than the proximal end. Also, the distal end of the tube 38 may be beveled radially inwardly in the distal direction as shown in FIG. 2 to provide a smooth outer surface at the juncture of the tube and tip for reducing hemolysis.

Catheter tip 40 includes a cylindrical proximal end portion 46 having an outer diameter sized to closely fit within the distal end 42 of tube 38, as seen in FIG. 2. End portion 46 of the tip serves as a connector which may be fixed within the bore or lumen 50 of catheter 38, such as by applying a cement or otherwise bonding the connector 46 to the sidewalls of lumen 50.

Referring also to FIGS. 3-6, connector 46 has a bore 48 connected in fluid communication with lumen 50 of tube 38 when in the assembled condition, such as shown in FIG. 2. An annular, radially outwardly extending, flange or ring 52 is integrally connected to the distal end of connector 46 and has a greater outer diameter than that of the connector so as to provide a radial shoulder 54 which engages the distal end of tube 38. Integral with and extending longitudinally from the ring 52, are four bars or struts 56, 58, 60 and 62. The struts are shown circumferentially or angularly equally spaced to provide four windows or openings 64. Tip 40 may have a lesser or greater number of struts and windows than are shown and described. The main portions of the struts are equally radially spaced from and extend parallel to the longitudinal axes of tube 38 and the tip 40. The distal ends of the struts smoothly curve radially inwardly and are integrally connected to a distal tip end 65 having a smoothly rounded distal outer end surface indicated generally at 66. As clearly seen in FIG. 4, the distal end 65 is generally circular and has an outer diameter that is less than that of the bore 48 and inner diameter of the ring 52 so that some blood can flow in a straight line path through tip 40.

As best seen in FIGS. 4 and 5, each of the struts 56-62 is smoothly contoured or rounded on its radially outer surface to reduce flow resistance and hemolysis, and the radially inner corners are also smoothly rounded to reduce hemolysis. Thus, the struts have a smoothly contoured periphery throughout their length and are free of any sharp edges. The outer surfaces of the struts smoothly blend into the outer surface of ring 52 as well as the outer surface of distal end 65. Also, the leading or distal surface 67 of ring 52, as best seen in FIGS. 3, 4 and 6, is smoothly contoured or rounded. The ring is rounded at both the radially inner and outer corners of the distal surface 67 to reduce hemolysis.

Catheter tip 40 also has a generally cone-shaped member or cone 70 having its base integrally connected to the inner side of distal end 65 of the tip. The outer surfaces of the cone and distal end 65, as best seen in FIGS. 3 and 6, join in a smoothly curving or round juncture so as to avoid blood cell hemolysis and flow restrictions. The cone 70 extends distally with its longitudinally extending vertical axis and apex, indicated at 72, coincident with the longitudinal axes of the tip 40 and tube 38. Cone 70 is circular in cross-section and its apex is smoothly contoured or rounded. The cone tapers radially inwardly in the proximal direction, the direction in which blood flows through the tip 40, as will be discussed hereafter.

During an operation, for example, when the catheter 20 is conveying blood from superior vena cava 16 to the extracorporeal system 24, as shown in Fig. 1, venous blood flows longitudinally into the distal end 65 of tip 40. Blood flows against the rounded distal tip end surface 66, through windows 64 between the smoothly connected and rounded struts 56-62, into the bore 48, and then into lumen 50 of tube 38 to the circulation system 24. Because the distal end surface 66 is rounded and the cone 70 is smoothly inclined proximally, which is the direction of blood flow, these surfaces do not present a high resistance to blood flowing longitudinally and proximally in or externally of catheter tip 40. Blood flowing into the tip 40 can flow from the cage or strut portion into the cylindrical bore 48 without a high resistance to flow since this juncture, indicated at 74 in FIG. 3, is rounded. Also, the smoothly curved or contoured sidewalls of the struts 50-62 and rounded distal wall portions 67 of the ring 52 allow blood to engage and flow around these smooth or rounded surfaces with little resistance. Some blood can flow in a substantially straight axial or longitudinal direction through the tip 40. Thus, blood can flow into and about the tip 40 with less turbulance and hemolysis.

The cone 70 not only provides a low resistance to blood flow into the tip 40 and tends to reduce turbulence but it prevents a fluid-flow dead space on the inner side of the distal end 65 of the tip. Eliminating the dead space reduces the chance of causing initial stages of thrombosis that might otherwise occur where the cone 70 is not present and surfaces unwashed by blood are present during extracorporeal circulation.

Thus, with the cone 70 and the smoothly rounded surfaces as described above, pressure drops and hemolysis of blood, as well as the chance of initial thrombosis are substantially reduced while the struts tend to prevent collapse or occlusion of the catheter by the sidewalls of the vena cava.

Catheter 20 has a single stage of blood entry and may be used with a second such catheter where total venous blood is to be drained from the vena cavae into the extracorporeal system as in the system shown in FIG. 1. However, catheter 20 may be used to deliver only a portion of the blood from the vena cava in which it is inserted where desired and when the particular surgery or operation permits.

In FIG. 7, a dual stage vena caval catheter 80 is shown which includes a tube 82 having a catheter tip 84 connected to the distal end of the tube. Catheter tip 84 is identical to catheter tip 40 of FIG. 2. Catheter tube 82 has a distal end portion 85 which is tapered radially inwardly toward the distal end and is provided with a plurality of inlet openings or holes 86. Tube 82 will generally have a larger lumen than that of catheter 20. Catheter 80 may be used as a two stage venus return catheter where of all of the vena cavae blood is not required to by-pass the right atrium, for example, during certain operations on blood vessels externally of the heart.

Catheter 80 may be inserted through an opening provided in the atrial appendage and be sealingly secured thereto by conventional purse string sutures. The tip 84 of catheter 80 may extend into the inferior vena cava while the entrance holes 86 are disposed in the right atrium. In such a procedure, the catheter is arranged so that blood from the inferior cava flows upwardly into the tip 84 of the catheter and between the catheter and walls of the vena cava toward the right atrium while blood from the superior vena cava flows down into the right atrium and into the holes 86. The proximal end of tube 82 may be connected to an extracorporeal system such as system 24, for example, by connecting the proximal end of catheter 80 to tube 28. In this case, for example, only a portion of the blood from the vena cavae flows into tube 28 of the system.

Since the construction of tip 84 is identical to that of tip 40 of FIG. 2, the same desirable and advantageous effects previously described in connection with the catheter 20 are provided by catheter 80. That is, because of the described smoothly curved or rounded surfaces and relative dimensions described above in connection with tip 40, the blood that flows into and around the catheter 40 or 80 tends to produce reduced pressure drops, reduced turbulence, and reduced hemolysis. Use of tips 40 and 84 tend to minimize or reduce the chance of initiating thrombosis sincethe cone allows blood to pass through the tip without creating a dead space or a blood free space on the proximal side of the distal end of the tip.

Catheter 80 is also shown to include a closure tube or obturator 88. Obturator 88 is a cylindrical plastic tube which when inserted into the tube 82 closes off communication between the tip 84 and the interior of tube 82. Obturator 88 is used during insertion of the catheter 80 into the right atrium so as to prevent initial blood flow into the catheter or tube 82 and out openings 86 until the openings are within the atrium. After completing the insertion of catheter 80, tube 88 is removed.

As various changes could be made in the above constructions without departing from the scope of the invention, it is intended that all matter contained in the above description and apparatus shown in the accompanying drawings be interpreted as illustrative and not in a limiting sense.

What is claimed is:

1. A catheter comprising an elongated tube, and a catheter tip including a proximal end portion connected to one end of said tube, a distal end portion having a smoothly contoured outer surface substantially symmetrical about the longitudinal axis of said tip, a plurality of curcumferentially spaced, longitudinally extending struts each connected at one end to said proximal end portion and at the opposite end to said distal end portion, and a generally cone-shaped member connected to the inner side of said distal end portion and tapering radially inwardly in the proximal direction with the apex of said cone-shaped member being substantially coincident with the longitudinal axis of said tip.

2. The catheter of claim 1 wherein each of said struts has an outer smoothly contoured periphery throughout the length of the strut 3. The catheter of claim 2 wherein said proximal end portion of said tip is generally cylindrical.

4. The catheter of claim 3 wherein said proximal end portion includes a ring integrally connected to the distal end thereof and having a smoothly contoured distal end surface, said ring being integrally connected to the proximal ends of said struts, and said struts being integrally connected at the distal ends thereof to said distal end portion.

5. The catheter of claim 1 wherein said tube tapers radially inwardly in the distal direction.

6. The catheter of claim 5 wherein said tube has a plurality of openings in the sidewall thereof.

7. The catheter of claim 1 wherein said tube has a distal end portion which tapers radially inwardly in the distal direction and a plurality of opening extending through the sidewall of said distal end portion of said tube.

8. The catheter of claim 1 wherein said plurality of struts include four struts forming a cage-like tip with four windows for the flow of blood proximally into said tip and with the outer surface of said distal end portion smoothly connecting with the outer surface of said cone-shaped member and the outer surface of each of said struts.

9. A catheter comprising an elongate tube, and a catheter tip including a generally cylindrical proximal end portion connected to one of said tube and including a ring integrally connected to the distal end of said proximal end portion and having a smoothly contoured distal end surface, a distal end portion having a smoothly contoured outer surface, a plurality of circumferentially spaced, longitudinally extending struts each having an outer smoothly contoured periphery throughout the length of the strut and integrally connected at one end to said ring and at the opposite end integrally connected to said distal end portion, and a generally cone-shaped member connected to the inner surface of said distal end portion and tapering radially inwardly in the proximal direction, the apex of said cone-shaped member being substantially coincident with the longitudinal axis of said tip, said outer surface of said distal end portion smoothly connecting with the radially outer surface of said cone-shaped member and the radially outer surface of each of said struts.

10. The catheter of claim 9 wherein the radially inner and outer corners of the distal side of said ring are smoothly rounded.

11. A vena caval venous blood return catheter for draining venous blood from a vena cava to an extracorporeal circulation system comprising a flexible tube having proximal and distal ends, the proximal end of said tube being adapted for connection in the extracorporeal circulation system, and a catheter tip for receiving blood flowing in the proximal direction into said tip when the catheter is in use and including a cylindrical connector portion at the proximal end thereof fixedly connected to the distal end of said tube, a ring integrally connected to the distal end of said connector portion, a generally annular distal end member having a smoothly contoured outer distal end surface symmetrical with the longitudinal axis of said tip, a plurality of generally longitudinally extending, circumferentially spaced struts integrally connected at their proximal ends to said ring and integrally connected at their distal ends to said distal end member to define a cage having a plurality of windows for the flow of venous blood proximally into said tip and tube, each of said struts smoothly curving radially inwardly adjacent the distal end thereof, said ring having smoothly curving distal wall portions, and a cone having its base connected to the inner side of said distal end member with its apex proximally spaced from said base and substantially coincident with the longitudinal axes of said tube and said tip, said outer surface of said distal end portion smoothly connecting with the outer surface of said cone-shaped member and the radially outer surface of each of said struts.

12. The catheter of claim 11 wherein said tube is formed of a plastic material.

13. The catheter of claim 12 wherein said catheter tip is of plastic material.

14. The catheter of claim 11 wherein said ring has an outer diameter substantially equal to the outer diameter of the distal end of said tube.

15. The catheter of claim 1 wherein said distal portion of said tube has a plurality of openings in the sidewall thereof.

16. The catheter of claim 11 wherein a distal portion of said tube tapers radially inwardly in the distal direction.

17. The catheter of claim 11 wherein said ring has an inner diameter greater than the outer diameter of said distal end member to provide straight line liquid flow through said tip.

18. The catheter of claim 17 wherein the outer diameter of said ring is substantially the same as the outer diameter of the distal end of said tube and wherein said distal end of said tube is engaged by said shoulder.

19. The catheter of claim 18 wherein the radially outer surface of each of said struts connects with the radially outer surface of said ring substantially in a smooth straight line fashion, and the radially inner surface of each of said struts smoothly connects with the radially inner walls of said connector portion.

20. A vena caval venous blood return catheter for draining venous blood from a vena cava to an extracorporeal circulation system comprising a flexible tube having proximal and distal ends, the proximal end of said tube being adapted for connection in the extracorporeal circulation system, and a catheter tip including a cylindrical connector portion at the proximal end thereof fixedly connected to the distal end of said tube, a ring integrally connected to the distal end of said connector portion and having a greater outer diameter than said connector portion to form a shoulder facing the distal end of said tube, a generally annular distal end member having a smoothly contoured outer distal end surface, a plurality of generally longitudinally extending, circumferentially spaced struts integrally connected at their proximal ends to said ring and integrally connected at their distal ends to said distal end member to define a cage having a plurality of windows for the flow of venous blood into said tip and tube, each of said struts smoothly curving radially inwardly adjacent the distal end thereof, said ring having smoothly curving distal wall portions, and a cone having its base connected to the inner side of said distal end member with its apex proximally spaced from said base and substantially coincident with the longitudinal axes of said tube and said tip, the apex of said cone being smoothly rounded, the outer surface of the base smoothly connecting with the outer surface of said distal end member, and said cone being circular in cross-section.

* * * * *